United States Patent [19]

Matsuura et al.

[11] Patent Number: 5,307,803
[45] Date of Patent: May 3, 1994

[54] DEFLECTING ENDOSCOPE

[75] Inventors: David G. Matsuura, Escondido; Curt Boyll, San Diego, both of Calif.

[73] Assignee: Intramed Laboratories, San Diego, Calif.

[21] Appl. No.: 845,630

[22] Filed: Mar. 4, 1992

[51] Int. Cl.$^5$ .............................. A61B 1/00
[52] U.S. Cl. .......................... 128/4; 138/118
[58] Field of Search ............ 128/4, 4 SM, 5, 6, 772; 138/118, 113, 178; 604/95, 280

[56] References Cited

U.S. PATENT DOCUMENTS

| | | | |
|---|---|---|---|
| 1,928,992 | 10/1933 | Clark et al. | 138/118 |
| 2,143,960 | 1/1939 | Stalter et al. | 138/118 |
| 4,420,016 | 12/1983 | Nichols | 138/178 X |
| 4,580,551 | 4/1986 | Siegmund et al. | 128/4 |
| 4,619,247 | 10/1986 | Inoue et al. | 138/6 |
| 4,686,963 | 8/1987 | Cohen et al. | 128/4 |
| 4,844,062 | 7/1989 | Wells | 128/6 X |
| 4,906,496 | 3/1990 | Hosono et al. | 128/113 X |
| 4,919,112 | 4/1990 | Siegmund | 128/4 |
| 4,942,866 | 7/1990 | Usami | 128/4 |

*Primary Examiner*—Richard J. Apley
*Assistant Examiner*—Karen A. Jalbert
*Attorney, Agent, or Firm*—Freilich Hornbaker Rosen

[57] ABSTRACT

An endoscope including a flexible shaft having a distal end which can be deflected by a manually operable mechanism on a handle assembly. The shaft includes an elongate member having longitudinal fins that extend radially outward. A hollow lumen through the core member forms a fluid channel, and the radially extending fins provide channels for accommodating optical fibers and pull wires. The member has a substantially continuous cross-section enabling it to be inexpensively extruded.

12 Claims, 4 Drawing Sheets

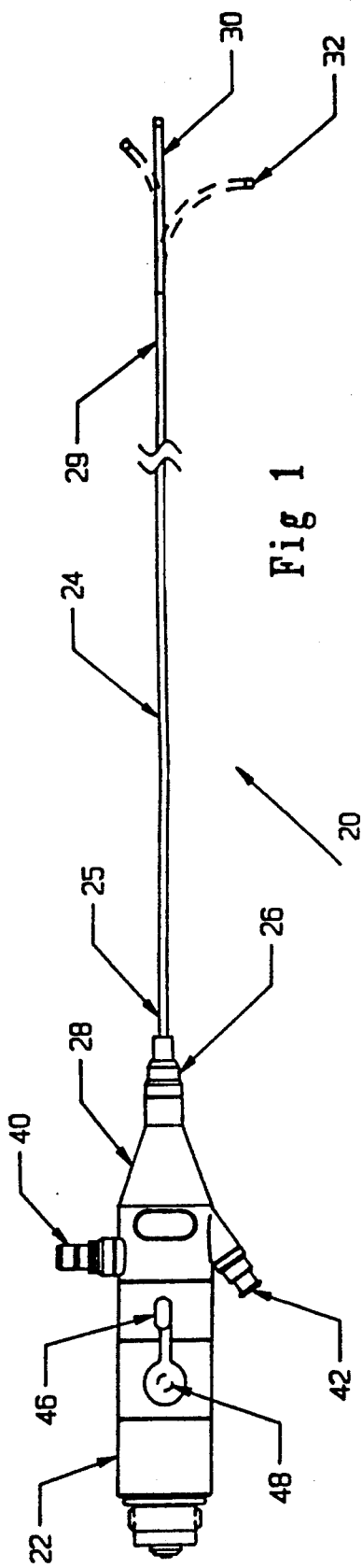
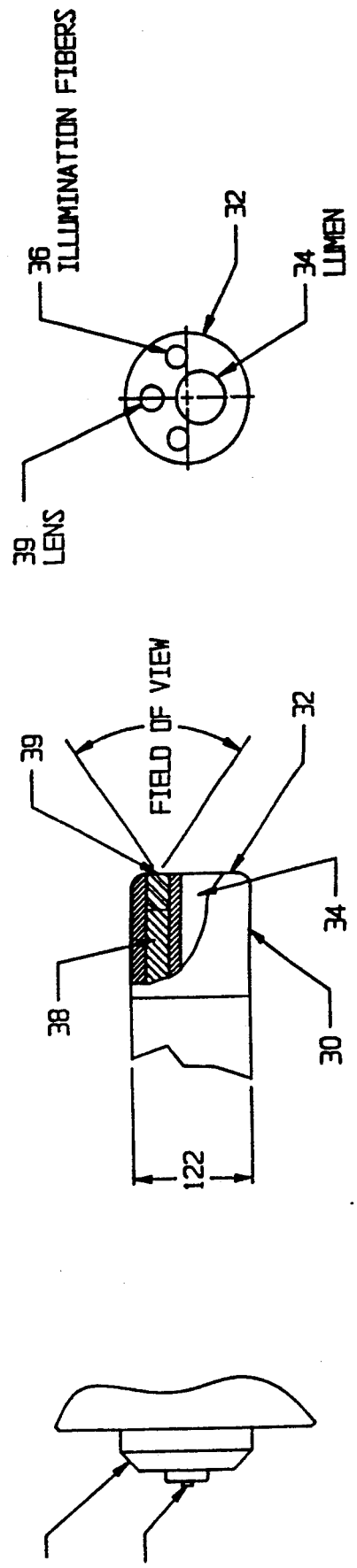
Fig 1
Fig 3A
Fig 3B
Fig 2

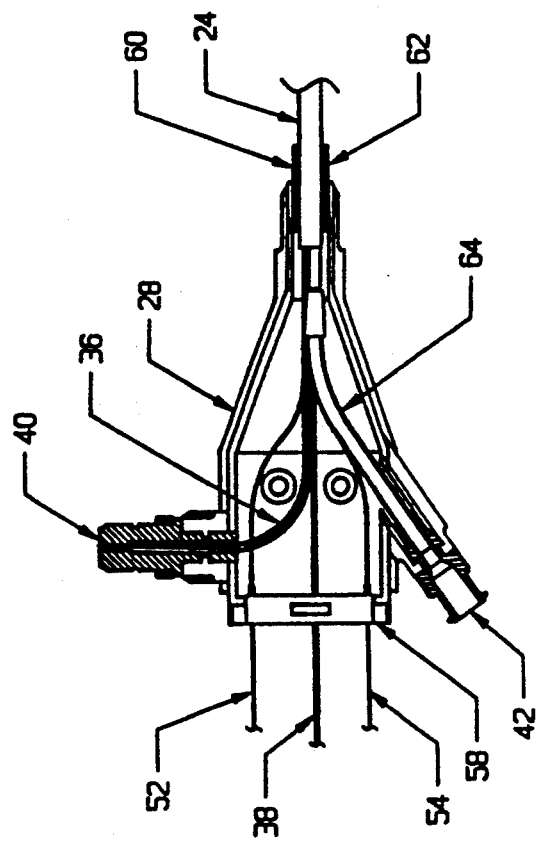
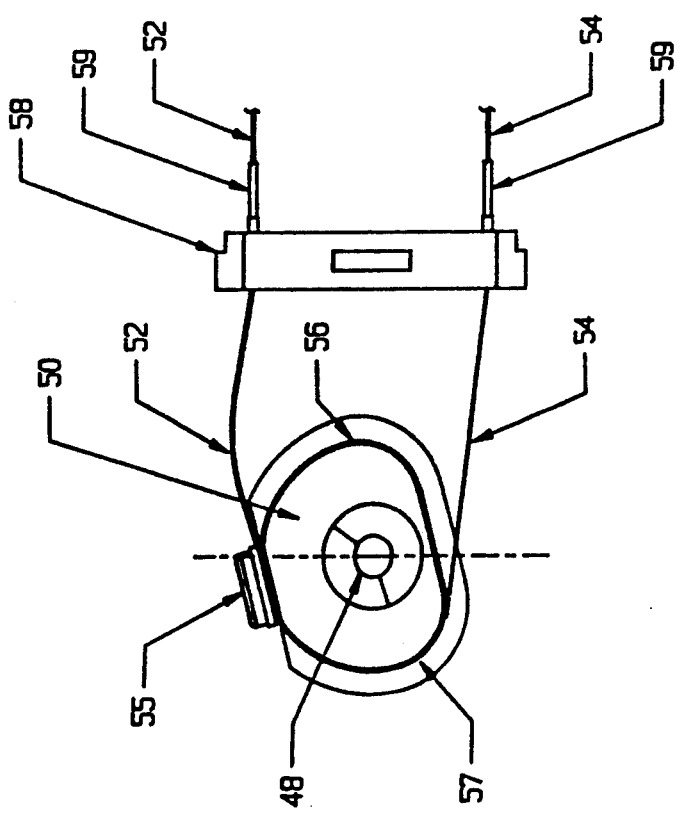
Fig 5
Fig. 4

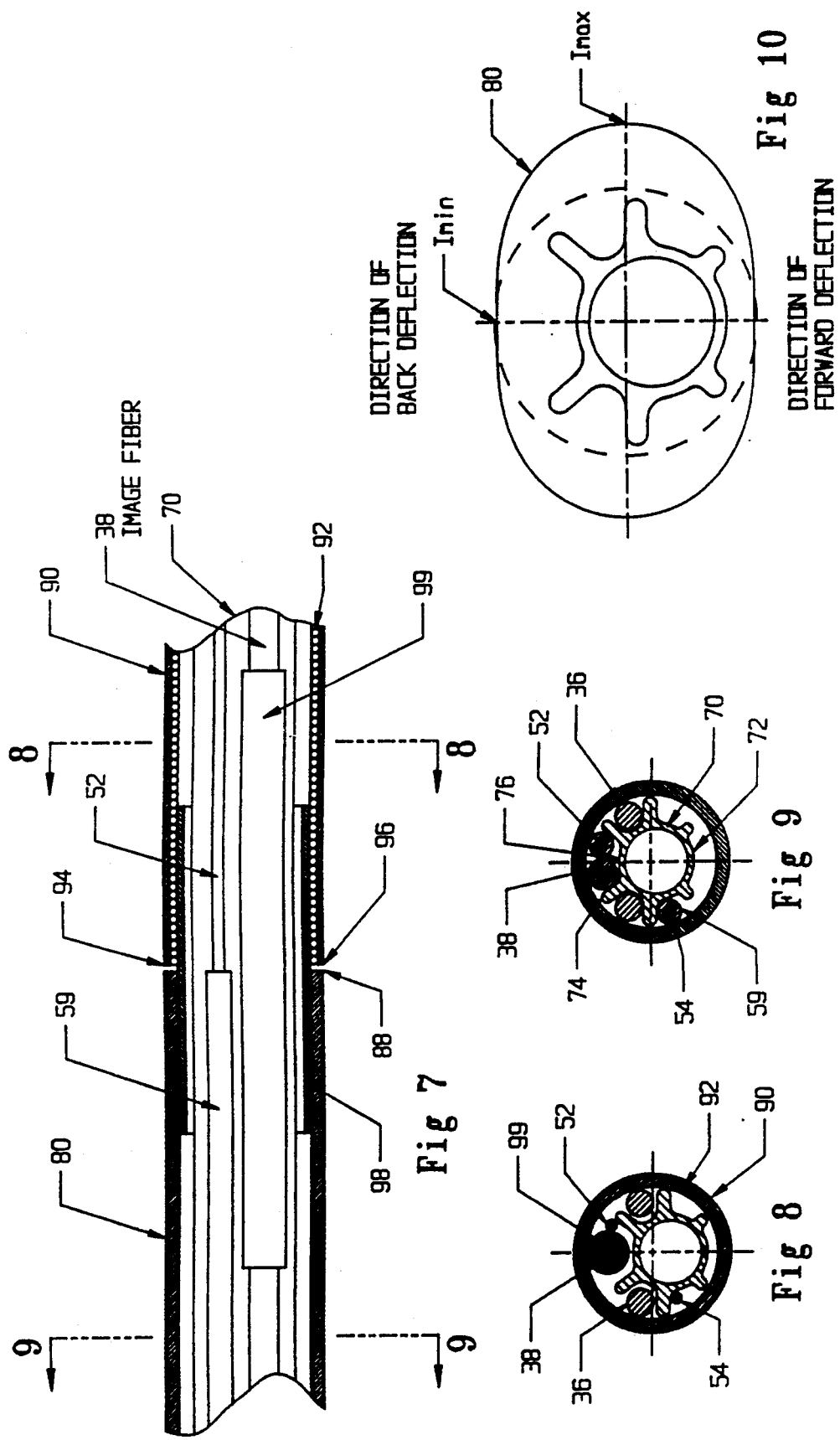

DEFLECTING ENDOSCOPE

BACKGROUND OF THE INVENTION

The present invention relates to a flexible shaft assembly whose distal end can be controllably deflected (or steered) by a control member located at the assembly's proximal end. Embodiments of the invention find utility in medical applications, e.g., as endoscopes and catheters, and in industrial applications, e.g., as endoscopes and various articulated mechanisms.

In a preferred embodiment of the invention, the flexible shaft assembly is configured for use as a medical endoscope incorporating illumination and imaging fibers, and a working lumen all extending from its proximal to its distal end, and all capable of being contained within a very small outside diameter, e.g. on the order of 3.0 mm or less. Such configurations are useful for example, as ureteroscopes, hysteroscopes, angioscopes, choledochoscopes, and cystoscopes.

The prior art is replete with flexible shaft endoscopes which incorporate a distal end which can be deflected by a user via a control member located at the shaft's proximal end. Such endoscopes are characterized by various shaft configurations which, for example, may make use of a multiplicity of vertebrated annuli or a tube with a series of transverse slots, configured to establish a moment of inertia profile which enhances the propensity of the shaft's distal end to bend in a controlled fashion in a defined plane. These shaft structures, by their nature, are complicated and costly to fabricate and are not particularly well suited for containment within very small outside diameters. The following patents are exemplary of deflectable shaft endoscopes:

| | |
|---|---|
| 5,005,558 | Aomori |
| 4,919,112 | Siegmund |
| 4,911,148 | Sosnowski |
| 4,653,476 | Bonnet |
| 4,580,551 | Siegmund |
| 4,577,621 | Patel |
| 4,534,339 | Collins |
| 4,353,358 | Emerson |
| 3,788,304 | Takahashi |

SUMMARY OF THE INVENTION

The present invention is directed to a flexible shaft assembly characterized by an elongate flexible member having a substantially continuous cross-section, thus enabling the member to be inexpensively extruded. The geometry of the member, including the utilization, for example, of longitudinal fins (or splines) is selected to establish a desired nonuniform moment of inertia profile around the member so as to define at least one preferred bending plane.

In a preferred embodiment, the elongate flexible member has a cross-sectional geometry defined by a cylindrical wall enclosing a hollow lumen and having spaced longitudinal fins projecting substantially radially outward from the wall. The hollow lumen is useful for passing fluid and/or tools and the spaced fins define longitudinal channels useful for accommodating multiple fibers (e.g. illumination and imaging) and pull wires extending from the proximal to the distal end of the flexible member. The cylindrical wall and fins are preferably integrally formed by a suitable extrusion process.

A preferred endoscope embodiment in accordance with the invention is comprised of a flexible shaft subassembly coupled to a handle subassembly. The handle subassembly provides suitable terminations for the proximal ends of the illumination and imaging fibers and pull wires. The handle subassembly includes a user operable control member, e.g. a crank, which can be manipulated to pull either of two pull wires, each distally connected to the distal end of the flexible member but displaced from one another and from the central axis of the member, to deflect the member's distal end along a defined bending plane.

In accordance with a further aspect of the preferred embodiment, the finned flexible member is jacketed by a thin flexible tube extending around the channels and their contents, i.e. fibers and wires.

In accordance with a still further aspect of the preferred embodiment, a resilient tubular member, e.g., a coil spring, is mounted around the distal end portion of the flexible member acting as a housing to resist transverse loading while still allowing the end portion to deflect in a preferred bending plane in response to tension on one of the pull wires.

Embodiments of the invention find particular utility as cost effective, single-use, miniature endoscopes for minimally-invasive surgery, diagnosis and treatment monitoring. For example only, embodiments of the invention having shaft outer diameters on the order of 3.0 mm are useful as angioscopes for viewing the interior of arteries and veins.

BRIEF DESCRIPTION OF THE DRAWINGS

FIG. 1 is a top plan view of an endoscope in accordance with the present invention;

FIG. 2 is an enlarged top plan of a portion of the proximal end of the handle subassembly of the endoscope of FIG. 1;

FIG. 3A is an enlarged side view of the distal end portion of the endoscope shaft subassembly and FIG. 3B is an end view of the shaft distal end face;

FIG. 4 is a plan view showing the connection of first and second pull wires to a crank arm mounted in the handle subassembly;

FIG. 5 is a sectional view of a portion of the handle subassembly;

FIG. 7 is an enlarged sectional view showing the internal construction of the shaft subassembly of FIG. 6 adjacent the junction between the shaft's main body and its distal end portion;

FIG. 8 is a sectional view taken substantially along the plane 8—8 of FIG. 7;

FIG. 9 is a sectional view taken substantially along the plane 9—9 of FIG. 7; and FIG. 10 is a schematic representation depicting the moment of inertia profile around the shaft subassembly flexible member.

DETAILED DESCRIPTION

Figure 6:
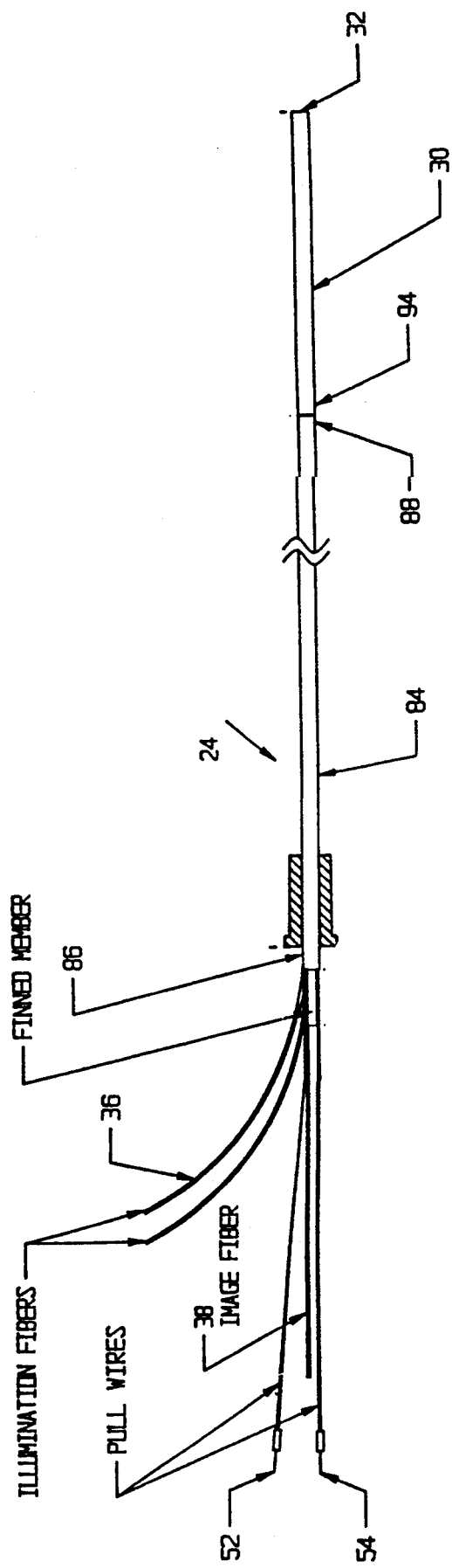
FIG. 6 is a top view of the shaft subassembly.

Attention is initially called to FIG. 1 which illustrates a preferred embodiment of a medical endoscope 20 in accordance with the present invention. The endoscope 20 is intended primarily, but not necessarily, for single use or disposable applications. It is comprised essentially of a handle subassembly 22 and a flexible shaft subassembly 24. As shown, the proximal end 25 of the shaft subassembly 24 extends into the distal end 26 of a handle body 28. The shaft subassembly is comprised of a main body portion 29 and a distal end portion 30 intended for insertion into a human body via an incision or orifice to enable a physician to illuminate and view the interior of a human organ.

FIG. 3B comprises a plan view of the distal end face 32 of the shaft subassembly 24 showing an open working lumen 34 terminating at the end face 32. Note, also, that the distal end of first and second illumination fibers 36 and image fiber 38 (terminated by lens 39) terminate at the end face 32.

The lumen 34, the illumination fibers 36, and the image fiber 38, all extend through the shaft subassembly 24, as will be discussed hereinafter, and have their proximal ends terminating within the handle subassembly 22. More specifically, the proximal ends of the illumination fibers 36 are coupled to a mount 40 which extends externally from the handle body 28 for coupling to an illumination source (not shown). The proximal end of the lumen 34 is coupled to a fluid fitting 42 which enables a fluid source to be coupled to the lumen 34 for supplying fluid to the distal end of the shaft subassembly 24. Further, the proximal end of the image fiber 38 terminates in an optical assembly mount 44 enabling a user to view the image field adjacent the distal end face 32.

Also extending externally from the handle body 28 is a user operable crank 46 mounted for limited pivotal movement about the axis of shaft 48. As will be seen hereinafter, clockwise movement of the crank 46 functions to deflect the shaft distal end portion 30 in one direction, while counter clockwise movement of the crank 46 deflects the shaft distal end portion in the opposite direction (respectively represented in dashed lines).

FIG. 4 depicts how manipulation of the crank 46 (FIG. 1) deflects the distal end portion of the shaft subassembly 24. The crank 46 is mounted on shaft 48 which in turn is mounted for limited rotation around its axis. The shaft 48 carries cam 50 which has first and second pull wires 52 and 54 secured thereto by screw 55. The wires 52, 54 extend around the surfaces 56, 57 of cam 50, through bulkhead 58, and then through sleeves 59 in the shaft subassembly 24. When the shaft 48 is rotated clockwise (as viewed in FIG. 4) pull wire 54 is drawn to the left (as viewed in FIG. 4) from its sleeve 59 and around cam surface 56. On the other hand, of course, when the shaft 48 is rotated counter clockwise, pull wire 52 is drawn to the left from its sleeve 59, around cam surface 56. These pull wires 52, 54, as shown in FIG. 5, extend through the forward portion of the handle body 28 and into the shaft subassembly 24. The distal ends of pull wires 52, 54 are securely terminated in the shaft distal end portion 30, close to the end face 32, respectively spaced oppositely from a shaft axis. The cam surfaces 56, 57 are preferably shaped to achieve a desired user crank force versus crank angle characteristic.

The proximal end of the shaft subassembly 24 is affixed to a bushing 60 which is mounted in the forward nose portion 62 of the handle body 28. FIG. 5 also shows the manner of connecting the fluid coupling 42 via a tube 64 to the working lumen 34 through the shaft subassembly 24. As can also be seen in FIG. 5, the illumination mount 40 projects from the handle body 28, for connection to the illumination fibers 36 extending through the shaft subassembly 24.

The present invention is particularly directed to improvements in the shaft subassembly 20 which enable it to be manufactured very inexpensively and to be constructed with a very small outer diameter, e.g. on the order of 3.0 mm. In accordance with the invention, and as best represented in FIGS. 8 and 9, the shaft subassembly 24 includes an elongate flexible member 70 which has a substantially continuous cross section, thus enabling it to be fabricated quite inexpensively, as by a suitable extrusion process. In accordance with the preferred embodiment, the elongate flexible member 70 is configured with a tubular or peripheral wall 72 which defines the aforementioned working lumen 34. A plurality of longitudinal fins 74 extend radially outward from the peripheral wall 72. The fins 74 are spaced from one another so as to define longitudinal channels 76 therebetween for accommodating the illumination fibers 36, the image fiber 38, and the pull wires 52, 54 (FIG. 8 and 9).

The cross sectional geometry of the elongate flexible member 70, including the dimensions and spacing of the longitudinal fins, is selected to establish a desired nonuniform moment of inertia profile around the member 70. This moment of inertia profile is represented by the plot 80 shown in FIG. 10. Note that it is oblong in shape having lower values (e.g. $I_{min}$) associated with certain directions of possible shaft deflection as compared to other directions (e.g. $I_{max}$). In the exemplary moment of inertia profile illustrated in FIG. 10, $I_{min}$ coincides with a vertical plane, and $I_{max}$ with a horizontal plane. The direction of lower moment of inertia, i.e., the vertical plane as depicted in FIG. 10, will be referred to herein as a preferred bending plane. By providing a nonuniform oblong shaped profile 80 as depicted in FIG. 10, the shaft distal end portion 30 will reliably deflect along a preferred bending plane responsive to tension on a pull wire 52, 54. By optimal placement of the fibers 36, 38 and wires 52, 54, the oblong shape of profile 80 can be even further enhanced.

Attention is now directed to FIG. 6 comprising a top view of the shaft subassembly 24 showing exemplary dimensions for an angioscope embodiment, and FIG. 7 showing the internal construction of the shaft subassembly 24 proximate to the junction 82 between the shaft main body portion 29 and distal end portion 30. Note in FIG. 6 that the illumination fibers 36, the image fiber 38, and pull wires 52, 54 are all depicted coming in from the left hand side and entering tubing 84 which extends through aforementioned bushing 60. The tubing 84 is mounted on and surrounds the elongate finned flexible member 70 over the length of the shaft body portion 29, jacketing member 70 and its longitudinal channels accommodating the aforementioned illumination fibers, image fiber, and pull wires. The tubing 84 extends from its proximal end 86 (FIG. 6) to its distal end 88 (FIG. 6), at the junction 94 with the shaft distal end portion 30. In lieu of extending tubing 84 the full length of finned elongate member 70, a thin wall oversleeve 90 and a resilient tube 92, e.g. a coil spring, are mounted around the elongate member 70 over the length of the distal end portion 30, shown in FIG. 6 as comprising 1.63 inches. An internal bushing 98 secures the tubing 84 to the coil spring 92. The function of the coil spring 92 is to act as a housing to resist transverse loading while still allowing the end portion 30 to deflect along a preferred bending plane in response to tension on one or the other of the pull wires 52, 54. Note that fiber 38 extends through a fixedly mounted loose sleeve 99 adjacent the junction 94 which allows for longitudinal movement of fiber 38 during flexure and thermal expansion.

From the foregoing, it should now be recognized that a flexible shaft assembly has been disclosed herein which allows for controlled tip deflection in single or multiple directions, within a very small outer diameter, and without requiring the use of vertebrated annuli or a transversely slotted tube. Rather, embodiments of the present invention employ a flexible elongate member having a cross-section selected to inherently define one or more preferred bending planes. Moreover, the member cross-section is substantially continuous over its length, thus allowing it to be fabricated via a low cost extrusion process. The disclosed preferred embodiment is comprised of an integrally formed member having a tubular wall carrying a plurality of outwardly projecting longitudinal fins. By appropriate selection of the size and placement of these fins, a desired moment of inertia profile is achieved to define one or more preferred bending planes. The fins additionally function to increase the compressive rigidity which prevents the elongate member from buckling when a pull wire is put in tension. The fins also provide radial support to resist kinking and collapse of the working lumen. Further, the fins also define the longitudinal channels which conveniently accommodate optical fibers and pull wires.

Although a preferred geometric cross-section comprised of a cylindrical wall and radially outward projecting fins has been described herein, it is recognized that other geometries having substantially continuous cross-sections are also capable of being extruded and defining a nonuniform moment of inertia profile in accordance with the invention. For example only, the fins could project radially inward from an outer wall. Alternatively, other geometries, such as various I beam cross-sections could be used.

We claim:

1. A flexible shaft assembly for use in a medical endoscope, including:
   an elongate flexible member having proximal and distal ends and a substantially continuous cross-section along its length, said flexible member comprising a peripheral wall defining a hollow lumen extending from said proximal end to said distal end;
   a plurality of longitudinal fins, each projecting radially from said wall to a free end, said fins extending along the length of said member and being dimensioned to establish a nonuniform moment of inertia profile around said member defining at least one preferred bending plane; and
   a pull wire extending from said member proximal end to said distal end for deflecting said member in said preferred bending plane.

2. The assembly of claim 1, wherein
   said fins project outwardly from said wall and are spaced from one another to define longitudinal channels extending along the length of said member.

3. The assembly of claim 2 wherein said pull wire is accommodated in a longitudinal channel defined between a pair of said plurality of fins.

4. The assembly of claim 3 further including at least one optical fiber extending from said member proximal end to said distal end accommodated in a longitudinal channel defined between a pair of said plurality of fins; and
   a jacket of flexible material mounted around said member surrounding said channels and the wire and fiber accommodated therein;

5. The assembly of claim 2 including a resilient tube mounted substantially coaxially around said member proximate to its distal end.

6. The assembly of claim 2 wherein said flexible member is integrally formed of substantially homogeneous material capable of being extruded.

7. An endoscope comprising:
   a handle body;
   a flexible shaft having a proximal end and a distal end, said shaft including a flexible elongate member comprising a peripheral wall defining a hollow lumen;
   a plurality of longitudinal fins, each projecting radially from said peripheral wall to a free end, said fins extending along the length of said member and being dimensioned and spaced to establish a nonuniform moment of inertia profile around said member defining at least one preferred bending plane;
   an optical fiber having a proximal end terminating in said handle body and a distal end terminating proximate to said shaft distal end, said fiber extending through a channel defined between a pair of said plurality of fins;
   a pull wire having a proximal end terminating in said handle body and a distal end terminating proximate to said shaft distal end, said pull wire extending through a channel defined between a pair of said plurality of fins; and
   a control member mounted on said handle body connected to said pull wire proximal end and selectively actuatable to pull said pull wire distal end toward said handle body to deflect said shaft distal end in said preferred bending plane.

8. The endoscope of claim 7 wherein said hollow lumen extends substantially axially through said elongate member and is open at said shaft distal end.

9. The endoscope of claim 7 including a resilient tube mounted substantially coaxially around said elongate member proximate to its distal end.

10. The endoscope of claim 7 including a jacket of flexible material mounted around said elongate member surrounding said channels and the wire and fiber extending therethrough.

11. The endoscope of claim 7 wherein said fins project outward from said wall.

12. The endoscope of claim 7 wherein said elongate member has a substantially continuous cross-section along its length and is formed of substantially homogeneous material capable of being extruded.

* * * * *